(12) United States Patent
Fox et al.

(10) Patent No.: US 11,918,300 B2
(45) Date of Patent: Mar. 5, 2024

(54) ULTRASOUND IMAGING SYSTEM PROVIDING NEEDLE INSERTION GUIDANCE

(71) Applicant: KONINKLIJKE PHILIPS N.V., Eindhoven (NL)

(72) Inventors: Shannon Renee Fox, Everett, WA (US); Changhong Hu, Bothell, WA (US); Kyong Chang, Mill Creek, WA (US); James Robertson Jago, Seattle, WA (US); Thanasis Loupas, Kirkland, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 139 days.

(21) Appl. No.: 16/963,859

(22) PCT Filed: Jan. 15, 2019

(86) PCT No.: PCT/EP2019/050844
§ 371 (c)(1),
(2) Date: Jul. 22, 2020

(87) PCT Pub. No.: WO2019/145183
PCT Pub. Date: Aug. 1, 2019

(65) Prior Publication Data
US 2021/0038320 A1 Feb. 11, 2021

Related U.S. Application Data

(60) Provisional application No. 62/620,512, filed on Jan. 23, 2018.

(51) Int. Cl.
*A61B 34/20* (2016.01)
*A61B 8/00* (2006.01)
*A61B 8/08* (2006.01)

(52) U.S. Cl.
CPC ............ *A61B 34/20* (2016.02); *A61B 8/0841* (2013.01); *A61B 8/4488* (2013.01); *A61B 8/463* (2013.01); *A61B 2034/2063* (2016.02)

(58) Field of Classification Search
CPC ............ A61B 2034/2063; A61B 34/20; A61B 8/0841; A61B 8/4488; A61B 8/463;
(Continued)

(56) References Cited

U.S. PATENT DOCUMENTS 6,193,659 B1 * 2/2001 Ramamurthy ...... G01S 15/8927
600/443
6,524,247 B2 2/2003 Zhao et al.
(Continued)

FOREIGN PATENT DOCUMENTS

JP 2004208859 A 7/2004

OTHER PUBLICATIONS

Junseob Shin et al., "Ultrasonic Reverberation Clutter Suppression Using Multi-Phase Apodization With Cross-Correlation," Nov. 2016, IEE Trans Ultrason Ferroelectr Freq Control, 63, 11, pp. 1947-1956 (pp. 1-29 on attachment) (Year: 2016).*
(Continued)

*Primary Examiner* — Joseph M Santos Rodriguez
*Assistant Examiner* — Maria Christina Talty

(57) ABSTRACT

An ultrasound imaging system for needle insertion guidance uses a curved array transducer to scan an image field with unsteered beams as a needle is inserted into the image field. Due to differences in the angle of incidence between the radially directed beams and the needle, echoes will return most strongly from only a section of the needle. This section is identified in an image, and the angle of incidence producing the strongest returns is identified. Beams with this optimal angle of incidence are then steered in parallel from the curved array transducer to produce the best needle
(Continued)

image. The steep steering angles of some of the steered beams can give rise to side lobe clutter artifacts, which can be identified and removed from the image data using dual apodization processing of the image data.

2 Claims, 7 Drawing Sheets

(58) Field of Classification Search
CPC ..... A61B 8/54; G01S 15/892; G01S 15/8927; G01S 7/52036
See application file for complete search history.

(56) References Cited

U.S. PATENT DOCUMENTS

| | | | |
|---|---|---|---|
| 6,786,870 B2 | 9/2004 | Miyaki et al. | |
| 6,951,542 B2 | 10/2005 | Greppi et al. | |
| 9,642,592 B2 | 5/2017 | Wang et al. | |
| 2002/0173721 A1* | 11/2002 | Grunwald | A61B 8/462 600/437 |
| 2013/0281834 A1 | 10/2013 | Tashiro | |
| 2014/0155738 A1* | 6/2014 | Cheny | A61B 8/0841 600/424 |
| 2015/0223776 A1 | 8/2015 | Ohuchi et al. | |
| 2016/0157828 A1* | 6/2016 | Sumi | G01N 29/46 702/189 |
| 2017/0020559 A1 | 1/2017 | Srinivasan et al. | |
| 2017/0084022 A1* | 3/2017 | Naidu | A61B 8/5223 |
| 2017/0108584 A1* | 4/2017 | Oelze | G01S 7/52047 |
| 2017/0143295 A1* | 5/2017 | Park | A61B 8/5207 |
| 2017/0184713 A1* | 6/2017 | Robert | G06T 7/0012 |

OTHER PUBLICATIONS

R. Schwann, N. Stache, T.G. Noll, "Optimization of Frequency Dependent Receive Apodization," 2005, IEEE Ultrasonics Symposium, pp. 1988-1991 (Year: 2005).*

Man M. Nguyen and Jesse T. Yen, "Performance Improvement of Fresnel Beamforming Using Dual Apodization With Cross-Correlation," Mar. 3, 2013, IEEE Transactions on Ultrasonics, Ferroelectrics, and Frequency Control, vol. 60, No. 3, pp. 451-462 (Year: 2013).*

International Search Report and Written Opinion for International Application No. PCT/EP2019/050844, filed Jan. 15, 2019, 16 pages.

* cited by examiner

ULTRASOUND IMAGING SYSTEM PROVIDING NEEDLE INSERTION GUIDANCE

RELATED APPLICATIONS

This application is the U.S. National Phase application under 35 U.S.C. § 371 of International Application No. PCT/EP2019/050844, filed on Jan. 15, 2019, which claims priority to Provisional Application Ser. No. 62/620,512, filed Jan. 23, 2018. These applications are hereby incorporated by reference herein.

This invention relates to medical ultrasound imaging systems and, in particular, to ultrasound systems which provide image guidance for insertion of biopsy needles and other invasive devices.

Ultrasound image guidance provides a simple and effective way to insert an invasive device such as a biopsy needle into the body. The imaging is used to view both the needle and the target anatomy in the body, and thus the clinician can see and plan the insertion path to the target as the needle is being inserted. Major blood vessels and obstacles to smooth insertion such as calcified tissues can be avoided. But obtaining a clear and complete image of the needle can be problematic due to the physics of ultrasound. During the procedure the clinician observes the target anatomy in the ultrasound image and then inserts the needle adjacent to the ultrasound probe in a direction aimed toward the target and passing through the image field of the probe. This path of travel can be at a relatively steep angle in relation to the ultrasound scanning beams. While a metallic needle is a strong reflector of ultrasound and thus presumed to show up clearly in the image, the steep angular relationship can cause the ultrasound energy to glance off and travel deeper into the body rather than be reflected directly back to the probe for image acquisition. Hence, the angular relationship between the needle shaft and the ultrasound beam direction can make needle imaging problematic. It is desirable to design the imaging system so that clear and complete images of a needle are obtained during insertion, so that the clinician can constantly know the location and position of the needle in the body.

The ultrasound beam angle can pose an additional impediment to clear and complete needle imaging, which is that returning echoes can be at steep angles relative to the probe aperture that give rise to grating lobe (side lobe) artifacts. These artifacts can appear in the image around the actual needle location in the image, making it difficult to discern the needle from the surrounding clutter. It is thus desirable to prevent or eliminate these clutter artifacts during needle insertion guidance.

In some aspects, the present disclosure includes methods for operating an ultrasonic imaging system for image guidance of needle insertion. The methods can include transmitting unsteered beams from an ultrasound transducer over an image field in a subject, identifying a peak angle of a transmit beam for producing a peak magnitude of echo returns from a needle in the image field, transmitting a plurality of parallel steered beams at the peak angle, and displaying an ultrasound image of the needle in the image field. In certain aspects, the methods can include identifying a line of needle specular reflections in the ultrasound image, and/or identifying a brightest point along the line of needle specular reflections. In some aspects, the identifying the angle of the transmit beam can include identifying the transmit beam which intersects the line of needle specular reflections at the brightest point, wherein the identified transmit beam further exhibits the peak angle. The displaying the ultrasound image of the needle can include displaying a needle guide graphic in the image, which can include displaying a graphic line at a location of the needle in the ultrasound image. The displaying the needle guide graphic can include displaying needle guide graphic lines on either side of a location of the needle in the ultrasound image. The displaying the needle guide graphic can include displaying graphic lines at the location of the needle in the ultrasound image and on either side of a location of the needle in the ultrasound image.

In some aspects, the present disclosure can include methods for operating an ultrasonic imaging system for image guidance of needle insertion that can include acquiring image data from an image field within a subject using a plurality transducer elements, wherein the image field is suspected of including a needle therein, processing the image data with two different apodization functions adapted to isolate clutter in the image data, using image data processed with the two different apodization functions to produce clutter-reduced image data, and displaying a clutter-reduced ultrasound image of a needle in the image field. The processing the image data with two different apodization functions can include forming two ultrasound images from the image data, each using a different apodization function. Using image data processed with the two different apodization functions can include combining or correlating image data from the two ultrasound images to produce clutter-reduced image data. Processing the image data with two different apodization functions can include processing the image data with complementary apodization functions. Processing the image data with complementary apodization functions can include processing the image data with apodization functions which affect side lobe artifact data differently. Processing the image data with apodization functions which affect side lobe artifact data differently can include using an apodization function which acts as a notch filter for side lobe or main lobe data. Using image data processed with the two different apodization functions can include combining image data with both side lobe and main lobe data with image data having only side lobe or main lobe data.

In accordance with the principles of the present invention an ultrasound system and probe with a convex curved array transducer are used for needle insertion guidance. The natural curvature of the array causes its unsteered beams to traverse a wide sector angle which extends beyond the footprint of the probe and quickly captures a needle during initial insertion. Images of the needle are analyzed to determine a point where the angle of incidence between an ultrasound beam and the needle shaft are best for needle image acquisition, and a needle image is acquired with beams steered in parallel from the curved array at the optimized beam angle. The needle location is indicated in the image with a needle guide graphic. The optimized beam angle is periodically updated during the procedure. In accordance with a further aspect of the present invention, clutter arising due to steep beam steering angles is reduced by producing images of a scan field with two different apodization functions, which are then compared or combined to reduce image clutter.

Figure 1:
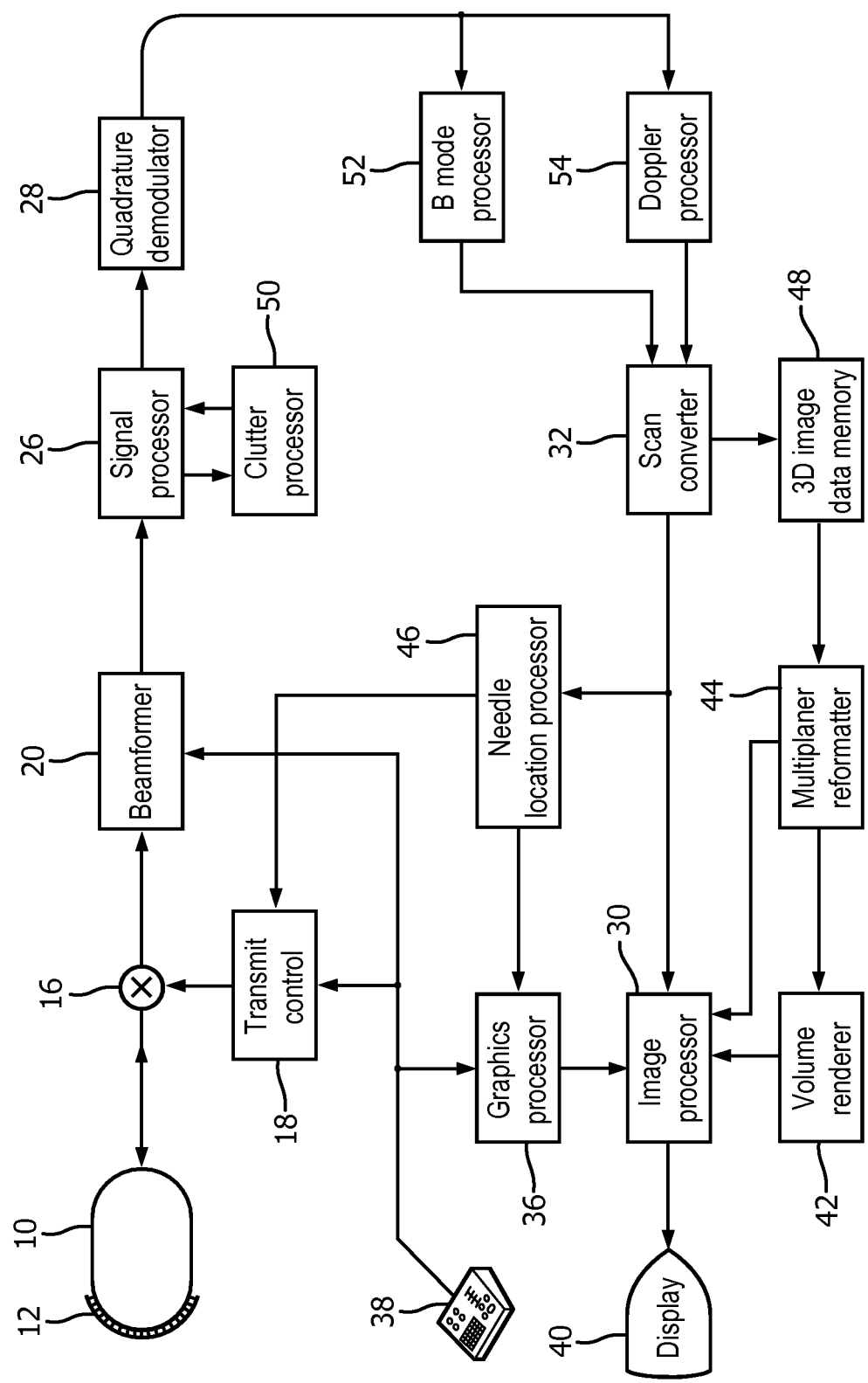
FIG. 1 illustrates an ultrasound system configured in accordance with the principles of the present invention.

Referring now to FIG. 1, an ultrasonic diagnostic imaging system constructed in accordance with the principles of the present invention is shown in block diagram form. A convex curved transducer array 12 is provided in an ultrasound probe 10 for transmitting ultrasonic waves and receiving echo information. The curved array transducer is coupled by the probe cable to a transmit/receive (T/R) switch 16 which switches between transmission and reception and protects the main beamformer 20 from high energy transmit signals. The transmission of ultrasonic beams from the curved array 12 is done under control of a transmit controller 18 coupled to the T/R switch and the beamformer 20, which receives input from the user's operation of the user interface or control panel 38. Among the transmit characteristics controlled by the transmit controller are the amplitude, phase, and polarity of transmit waveforms, as well as the focusing and steering of ultrasound beams effected together with beamformer control. Beams formed in the direction of ultrasound transmission may be unsteered (directions orthogonal to the face of the transducer), or steered at different angles relative to the face of the array. The echoes received by a contiguous group of transducer elements referred to as the active aperture are beamformed in the beamformer 20 by appropriately delaying them and then combining them to form a coherent echo signal.

The coherent echo signals undergo signal processing by a signal processor 26, which includes filtering by a digital filter and noise reduction as by spatial or frequency compounding. The signal processor can also shift the frequency band to a lower or baseband frequency range. The digital filter of the signal processor 26 can be a filter of the type disclosed in U.S. Pat. No. 5,833,613 (Averkiou et al.), for example. In accordance with one aspect of the present invention, a clutter processor 50 is coupled to the signal processor to remove sidelobe clutter arising during beam steering as described more fully below. The processed echo signals are demodulated into quadrature (I and Q) components by a quadrature demodulator 28, which provides signal phase information.

Figure 3:
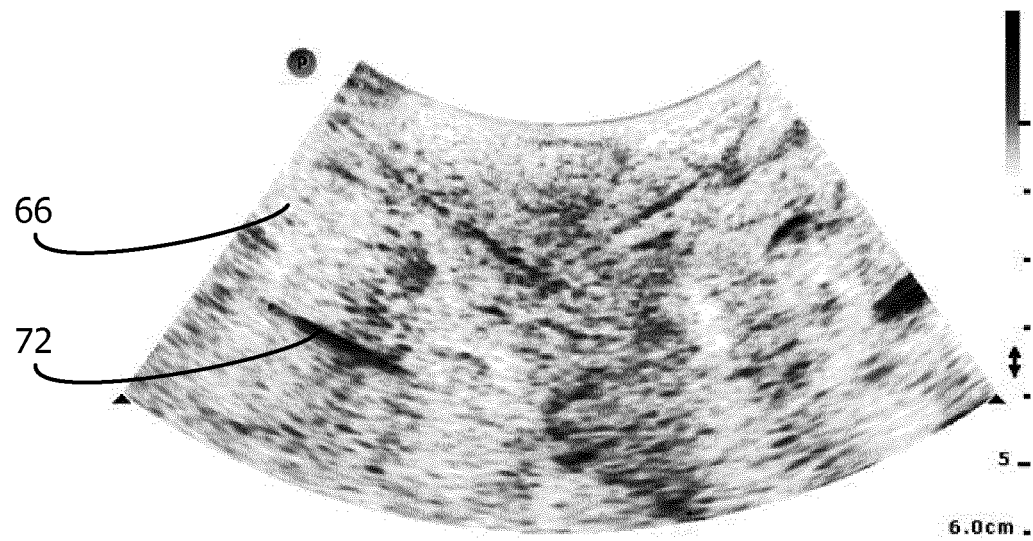
FIG. 3 is an ultrasound image of insertion of a needle into a subject at the insertion angle shown in FIG. 2.
Figure 5:
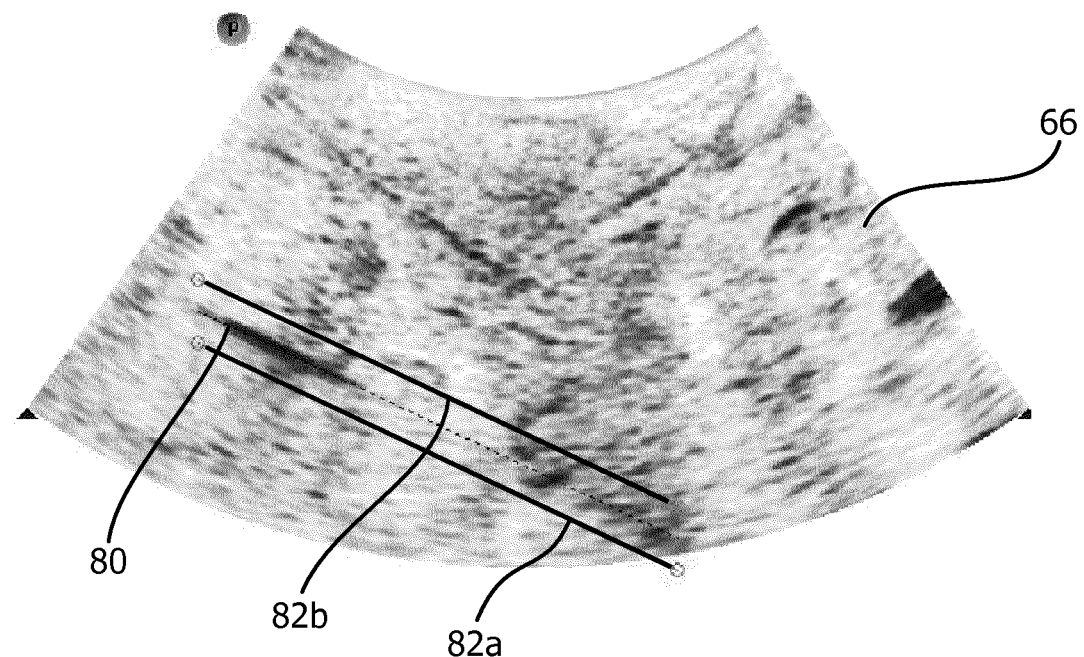
FIG. 5 is an ultrasound image of a needle with its location indicated by a needle guide graphic.

The beamformed and processed coherent echo signals are coupled to a B mode processor 52 which produces a B mode tissue image. The B mode processor performs amplitude (envelope) detection of quadrature demodulated I and Q signal components by calculating the echo signal amplitude in the form of $(I^2+Q^2)^{1/2}$. The quadrature echo signal components are also coupled to a Doppler processor 54, which stores ensembles of echo signals from discrete points in an image field which are then used to estimate the Doppler shift at points in the image with a fast Fourier transform (FFT) processor. For a color Doppler image, the estimated Doppler flow values at each point in a blood vessel are wall filtered and converted to color values using a look-up table. The B mode image signals and the Doppler flow values are coupled to a scan converter 32 which converts the B mode and Doppler samples from their acquired R-θ coordinates to Cartesian (x,y) coordinates for display in a desired display format, e.g., a rectilinear display format or a sector display format as shown in FIGS. 3 and 5. Either the B mode image or the Doppler image may be displayed alone, or the two shown together in anatomical registration in which the color Doppler overlay shows the blood flow in tissue and vessel structure in the image.

The ultrasound image data produced by the scan converter 32 are coupled to an image processor 30 and a 3D image data memory. The image processor 30 performs further enhancement, buffering and temporary storage for display of an ultrasound image on an image display 40. The 3D image data memory stores image data values at addresses related to their coordinates in 3D space, from which they can be accessed for 3D image formation. The 3D image data memory is coupled to a multiplanar reformatter 44 and a volume renderer 42. The multiplanar reformatter converts echoes which are received from points in a common plane in a volumetric region of the body into an ultrasonic image of that plane, as described in U.S. Pat. No. 6,443,896 (Detmer). The volume renderer 42 converts the echo signals of a 3D data set into a projected 3D image as viewed from a given reference point as described in U.S. Pat. No. 6,530,885 (Entrekin et al.) The 2D or 3D images produced from 3D image data are coupled to the image processor 30. A graphic display overlay containing textual and other graphic information such as patient ID is produced by a graphics processor 36 for display with the ultrasound images.

Figure 2:
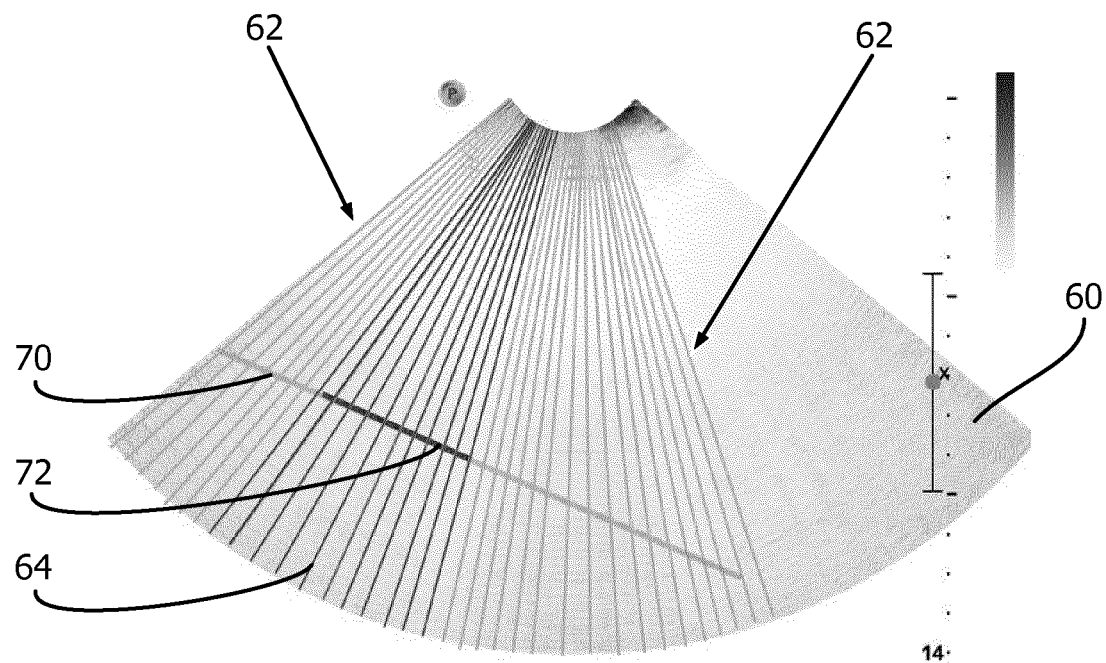
FIG. 2 illustrates the angles of incidence between a needle and unsteered beams from a curved array transducer.

FIG. 2 illustrates an image field 60 which is scanned by unsteered beams 62 transmitted and received by a curved array transducer. The beams are unsteered because their directions are determined by the curved geometry of the array; each beam is directed normal to its point of origin along the face of the array. In beam formation, unsteered beams are formed by equally weighting echoes received at symmetrical locations of the active aperture on either side of the point of origin. The beams have a symmetrical weighting profile in the beamformer. The same symmetrical weighting profile can be used to form each beam along the array, with the different angular directions of the beams provided by the geometrical array curvature. The natural curvature of the array thus causes each beam 62 to be directed at a different angle across the image field, thus scanning a sector-shaped field 60. This is advantageous for needle insertion imaging, as only a single weighting table needs to be loaded into the beamformer for scanning and echo formation along each different beam direction. The broad sector image field is advantageous for needle insertion imaging, since the needle is inserted into the body at the side of the probe, and in line with the scan plane. The needle is quickly acquired at the edge of the wide image, as it will begin to intersect beams at the side of the sector after just a few millimeters of insertion.

But the angle of the inserted needle relative to the beam angles will cause different degrees of echo detection from different transmit beams depending on the angle of incidence of the beams impinging upon the needle. In the illustration the beams intersecting the needle 70 before and after the central darkened section 72 are at non-orthogonal angles relative to the needle shaft. Echoes from these beams will scatter in directions away from the beam path, and less of their energy will return to the array elements. The darkened beams on either side of beam 64 are more orthogonal to the shaft of needle 70, causing more of their energy to be reflected back directly to the array. The beam 64 is most optimal as it is nearly orthogonal to the needle at its point of intersection and echoes from this beam will most strongly return to the array from the specular reflecting needle. Thus the section 72 of the needle which produces these stronger echo returns will appear most distinctly in the ultrasound image, as clearly shown in the actual ultrasound image 66 of FIG. 3. (This image is shown with black-white display reversal for better illustration.)

Figure 4:
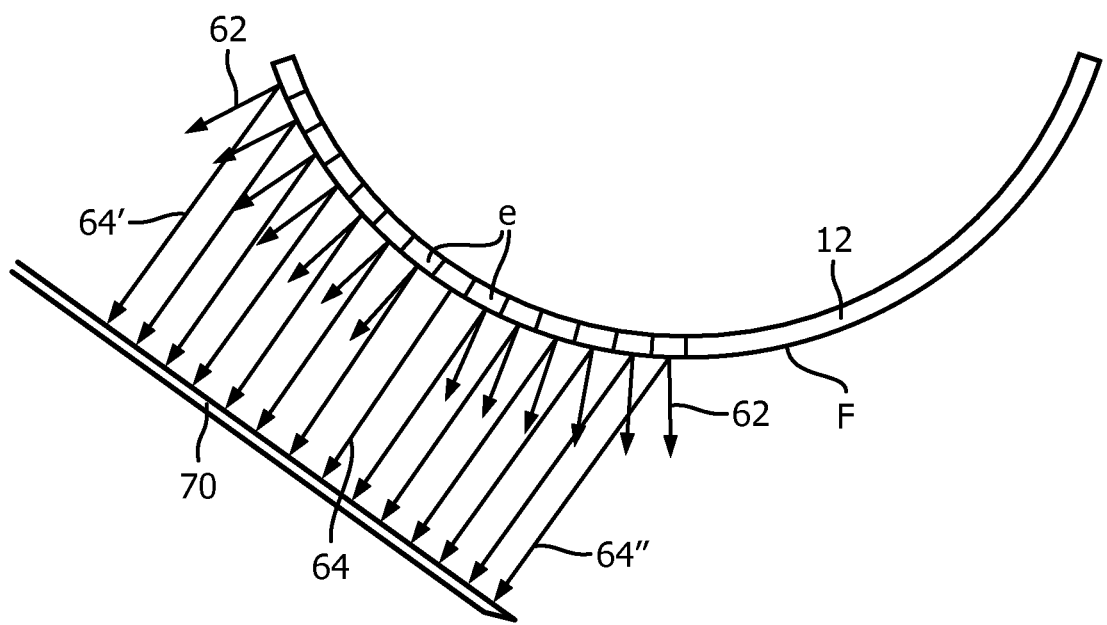
FIG. 4 illustrates acquisition of a needle image by steering beams in parallel at an optimal angle from a curved array transducer.

In accordance with the present invention, the ultrasound system includes a needle location processor 46 which identifies the distinct needle section 72 in the ultrasound image 66, and particularly the angle of the most optimal beam 64. The needle location processor uses image processing to search for and identify the straight line of strong echoes from needle section 72 in the image. This can be done using image processing techniques such as Hough transforms, Radon transforms, first- and second-order directional texture analysis, or heuristic criteria such as maximum brightness analysis. When this echo return section is identified in the image, the point along the section of the strongest echo return denotes the point where the optimal unsteered beam intersects the needle, and the identity of the beam is thus determined by simple geometry. With beam 64 thereby identified as the unsteered beam with the optimal angle for imaging the needle most strongly, the needle location processor commands the transmit controller 18 and beamformer 20 to transmit and receive steered beams from the array 12, all steered at the identified optimal angle of beam 64. This is shown in FIG. 4, where the array 12 is shown transmitting beams 64' . . . 64 . . . 64", all transmitted and received at the same angle relative to the needle 70, an angle which is nearly orthogonal to the needle. Also shown for comparison are arrows 62 depicting unsteered beam angles from the array 12. The steered beams 64' . . . 64 . . . 64" are seen to emanate from the same points along the face F of the array as the unsteered beams, but are steered by phased operation at different respective angles relative to the face F of the array which causes them to all be directed in parallel, and to impinge upon the needle at an orthogonal or nearly orthogonal angle. Imaging the needle with these parallel steered beams will produce relatively strong echo returns from the needle 70, and a sharper, clearer appearance of the needle in the ultrasound image.

Scanning with parallel steered beams from a curved array is a nonobvious use of a curved array. This is because a curved array has an inherent preferential radial scan pattern due to its curved geometry. A standard flat linear array, by comparison, has no inherent radial scan pattern. Its flat geometry has made it the array of choice for linear as well as phased beam steering. So-called "steered linear" scanning has long been performed by phased operation of flat linear arrays for color Doppler imaging, as exemplified by U.S. Pat. No. 5,014,710 (Maslak et al.), as has phased sector scanning. One skilled in ultrasonic imaging would choose a curved array specifically to take advantage of its natural radial scan pattern, not for use in steered parallel beam scanning. Not only is the curved array geometrically unsuited for this mode of operation; phased steering of beams from a curved array quickly gives rise to side lobe artifact clutter due to steep beam steering angles, as discussed in detail below.

When the needle location processor 46 has operated as described to locate the needle in the ultrasound image as just explained, it further commands the graphics processor 36 to overlay the ultrasound image 66 with a needle location graphic as shown in FIG. 5. Needle guidance systems of the prior art have generally positioned needle location graphics over the location of the needle itself, as shown by the dotted graphic 80 which is positioned over the needle location in the body. This can pose a difficulty, as the image of the needle is obscured by the graphic. Often, the clinician would prefer to have the needle in the image unobstructed, particularly around the needle tip, which the clinician is usually focused on most intently to guide the insertion. A preferred graphic which does not obstruct the needle in the image has graphic lines 82a and 82b which frame the image of the needle between them. The graphics 82a, 82b quickly identify the needle location for the clinician without obscuring the image of the needle or the needle tip. Some clinicians may prefer to use both graphics, with the lines 82a, 82b encompassing the needle location and a lighter or broken line graphic 80 specifically identifying the shaft of the needle in the image.

As needle insertion progresses, the direction of insertion can change as the clinician manipulates the needle to avoid piercing blood vessels or work around hard substances in the body. Since the needle orientation can change due to needle manipulation or probe movement, the image processing and optimal beam angle identification and beam steering are repeated periodically by the needle location processor 46, updating the steering angle of beams 64, 64' as needed to maintain the clearest image of the needle as can be afforded by the procedure.

An ultrasound array, like a radio antenna, exhibits an energy profile of the ultrasound energy transmitted or received by the array. This antenna pattern for an ultrasound array is known as a lobe pattern. The pattern has a main or central lobe which axially aligns with the beam direction, and side lobes which can also be sensitive to off-axis echo reception. In most instances, the clinician would prefer a strong, narrow main lobe in the beam direction, and virtually nonexistent side lobes. This is because energy received in side lobes in the image field can result in the production of artifacts in the image during beamformation, clutter which can obscure the image of the needle. The beamformer is programmed on the assumption that all energy is being received from along the beam axis. Off-axis energy received from the side lobes will be undesirably beamformed and manifest itself as artifacts in the resultant image. Side lobe clutter artifacts are prevented by using a probe with an element pitch (center-to-center spacing) which is less than half of the ultrasound frequency wavelength. When the beams of the curved array are unsteered, a half-wavelength element pitch will avoid the appearance of side lobe clutter. But when beams are steered at increasing nonorthogonal angles to the face of the array, side lobes become larger and the likelihood of side lobe artifacts increases, particularly in the case of a curved array where the array curvature causes the steered angles at the face of the array to be steeper than would be the case with a flat linear array. In FIG. 4 it is seen that the outermost needle imaging beams 64' and 64" are at significant nonorthogonal steering angles relative to the face F of the array 12, and these steeper steering angles can be a source of side lobe image clutter. In accordance with a further aspect of the present invention, side lobe clutter is reduced by a clutter processor 50 in the ultrasound system. The clutter processor 50 operates by forming two ultrasound images from the echoes produces from a scan of the image field, each using a different apodization function. The pixel values of the two differently apodized images are combined to reduce side lobe clutter artifacts in the final image.

Figure 6:
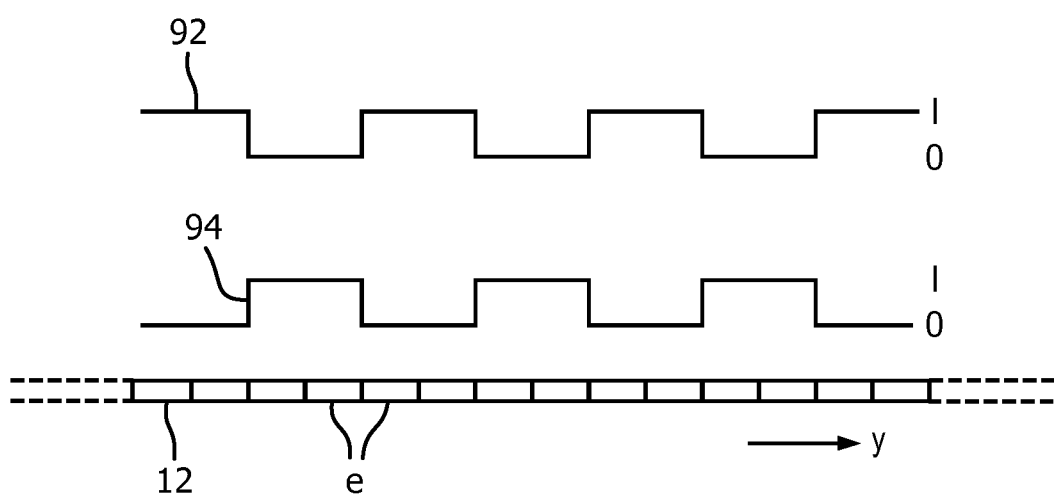
FIG. 6 illustrates a first dual apodization technique which can be used to reduce clutter arising due to beam steering in needle guidance imaging.

One set of apodization functions for clutter removal is shown in FIG. 6. At the bottom of the drawing is an array 12 of transducer elements e, extending in a direction y. Shown above the array 12 in spatial correspondence are two different apodization functions 92 and 94. One apodization function is used when beamforming the echo signals received from the image field to form a first image, and the other apodization function is used when beamforming the same echo signals to form a second image. It is seen that apodization function 92 weights the signals from two adjacent elements with a weight of one, then the signals from the next two elements with a weight of zero, then the next two signals with a weight of one, and so on. The apodization function 94 is the inverse, with the same alternation of one and zero weights across the aperture. The beamformed echo signals of the two images are amplitude detected, producing pixel values for the two images. Pixel values at the same spatial location in the two images are then compared or correlated. If the correlation of the two values is high, such as greater than 50%, one or both of the values are used for that pixel value in the resultant image. If the correlation of the two values is relatively low, such as less than 50%, the values are omitted from the image. That is because the main lobe signals processed by the two complementary apodization functions will be approximately the same, whereas signals from the side lobes on either side of the main lobe in the two images, the side lobes which are the greatest contributors of clutter, will be of opposite polarity and de-correlated. Thus, side lobe clutter is reduced in the resultant image. Since this processing is all done on a single image acquisition, there is no adverse effect on the frame rate of display. And since this clutter reduction processing uses amplitude detection, the resultant pixel values can be directly processed into a B mode image by the B mode processor 52.

Figure 7A:
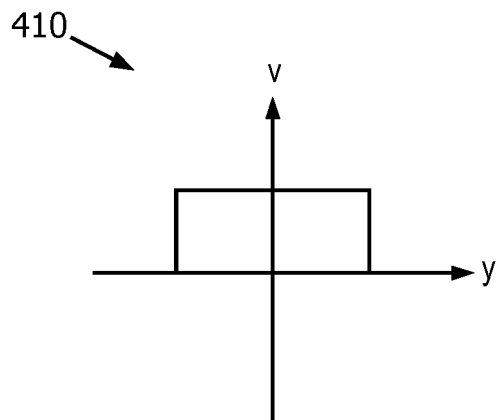
FIGS. 7a and 7b illustrate a second dual apodization technique which can be used to reduce clutter arising due to beam steering in needle guidance imaging.
Figure 7B:
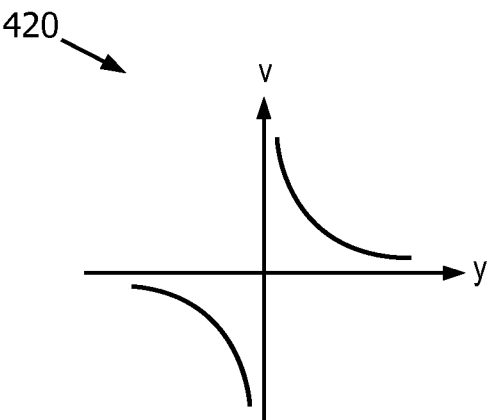

Preferred apodization functions for clutter reduction of needle images are shown in FIGS. 7a and 7b. The graphs of these two drawings are plotted as voltage weighting, v, against distance from the center of the ultrasonic transducer array, y. The graph 410 of FIG. 7a shows an example of a first apodization function in the form of a rectangular apodization function. This apodization function results in signals from all of the elements of the transducer array receive an equal weighting such as one. The results of applying this function to the received echo data are shown in FIG. 8a.

Figure 8A:
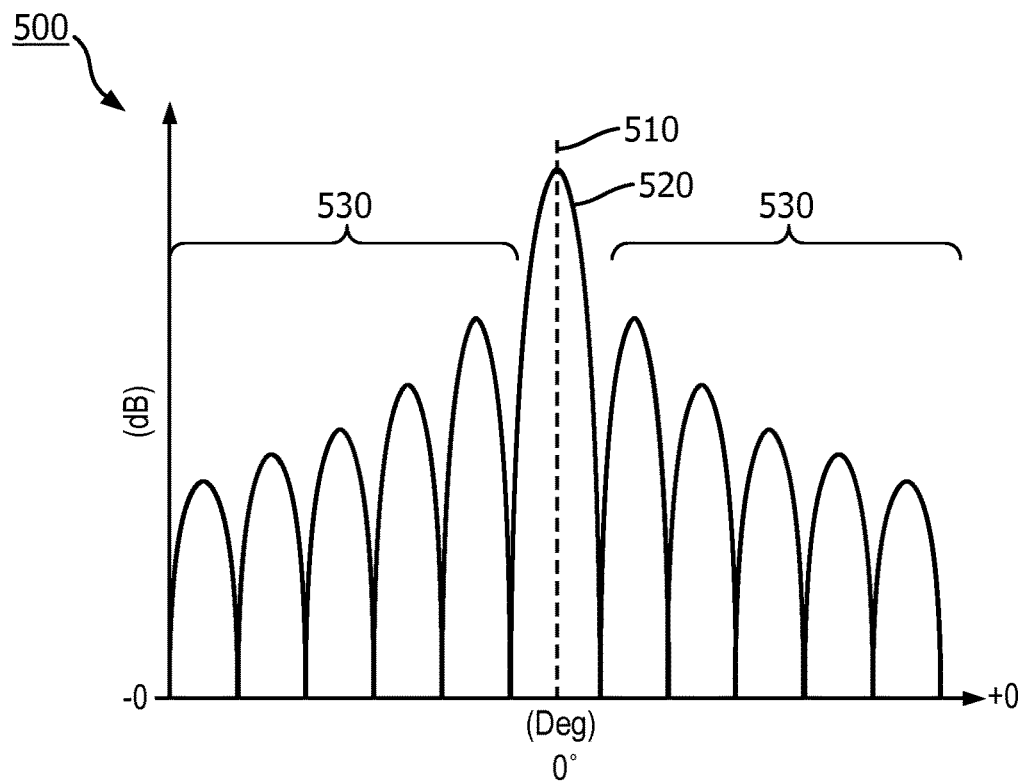
FIGS. 8a and 8b illustrate the sidelobe energy resulting from use of the two apodization functions of FIGS. 7a and 7b.

FIG. 8a shows a plot 500 of magnitude, measured in dB, against steering angle θ. The plot depicts the summation of all of the echo signals received by each transducer element of a transducer array, across all of the steering angles within the field of view of the array. More specifically, the plot shows the main and side lobe response in image data beamformed using the first apodization function 410 shown in FIG. 7a. This is the response characteristic of a standard unapodized B-mode ultrasound image, which has a high intensity response at a steering angle of 0° 510, the main lobe response 520. Signals from a steering angle of 0° arrive coherently at the transducer array and form the main lobe response of an image using uniform apodization function 410. Due to spatial resolution limitations, the main lobe 520 has a finite width that includes a small range of angles either side of zero degrees. Image data with this characteristic also includes multiple signals of diminishing intensity spreading out from the main lobe, the side lobes 530. The side lobes are the response of signals with a steering angle outside of the range of the main lobe.

Constructive and destructive interference effects at different angles create the peaks and troughs in the side lobes. The side lobes contribute the clutter in an ultrasound image, whereas the main lobe provides the desired signals from the ultrasound image target.

Figure 9:
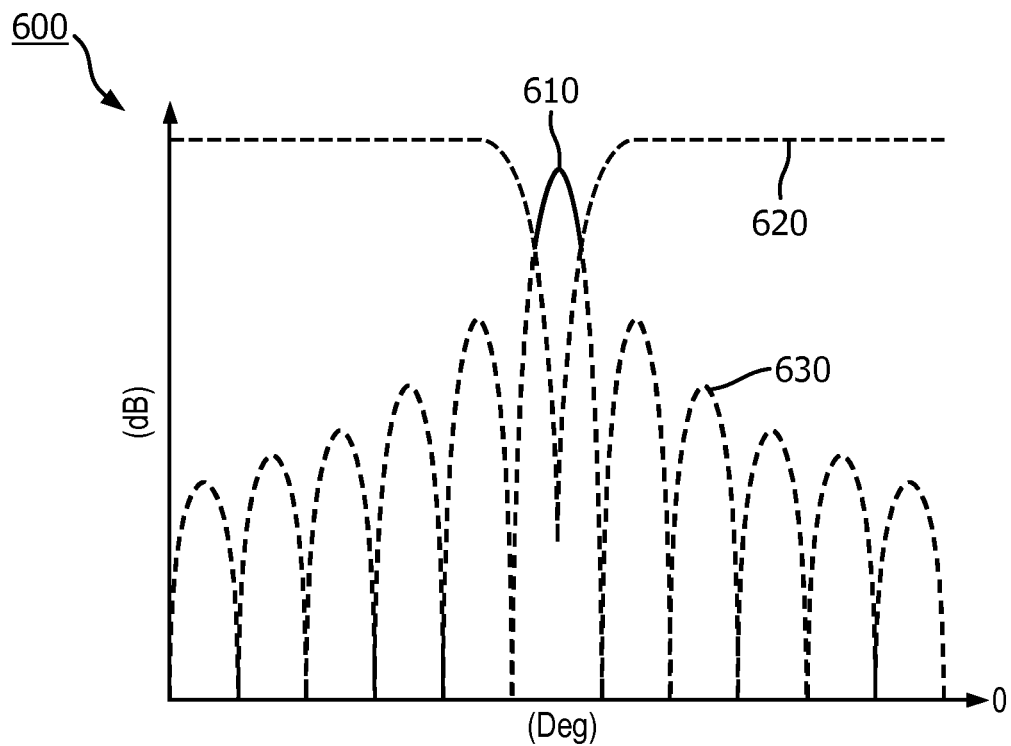
FIG. 9 illustrates the reduction of sidelobe clutter achieved by a combination of the two apodization functions of FIGS. 7a and 7b.
Figure 8B:
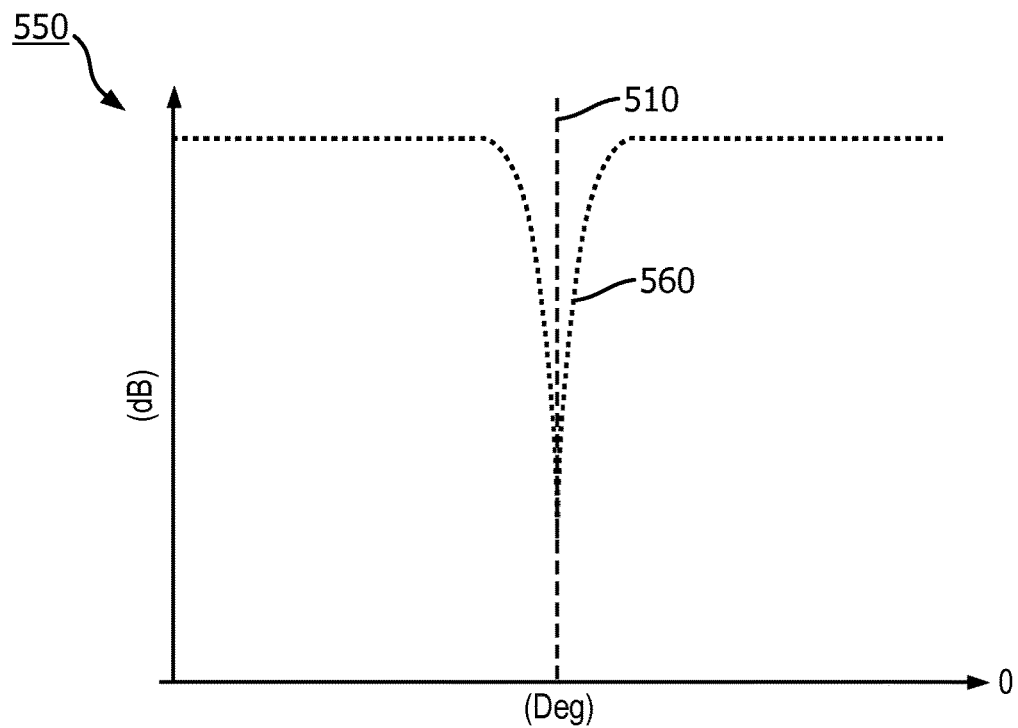

The second graph 420 of FIG. 7b shows an example of a second apodization function in the form of a reciprocal function, such as y=1/x, which is used to introduce a null point in the image data response as illustrated by plot 550 of FIG. 8b. When this notch filter is applied as a pass filter to the lobe characteristic 500, signals from the main lobe of the beampattern of the array receive a high weighting, which decreases exponentially towards signals from the more lateral side lobes. The results of applying this function to the received echo data are shown in FIG. 9. The shapes of the apodization functions used may be designed by the user of the ultrasound system or may be preloaded onto the system and selected by the user to perform a desired function. Once the shape of an apodization function has been selected or designed, it may be adjusted through a single control parameter. This parameter is a scaling factor, k, which may be empirically determined by the user through the use of the ultrasound system.

Linear acoustics dictates that the ultrasound beampattern is equivalent to the Fourier transform of the apodization function used. This relationship provides a tool for analysis and beampattern design. More specifically, it is possible to design the apodization function to achieve a desired beampattern. For example, the image data produced by use of the apodization function 420 will exhibit a sharp null at the main lobe location and a decreased amplitude at off-axis steering angles, as shown in FIG. 8b. The Fourier transform relationship between the apodization function 420 and the beampattern of the second image data can be used to discern what type of apodization function should be used to achieve the desired beampattern.

By applying the reciprocal second apodization function 420 to the echo signal data, a null 560 is generated at the same steering angle as the main lobe 520 of the image data processed using apodization function 410. In this example, the second apodization function 420 is acting as a notch filter; however, depending on the application, many different shapes of apodization function may be utilized.

FIG. 9 shows a plot 600 depicting a superposition of the plots from FIGS. 8a and 8b, which depict the image data resulting from use of the first and second apodization functions 410 and 420, respectively, for an image pixel. By comparing pixels of the first and second images processed by the apodization functions, the minimum signal magnitude across the steering angles can be found. This is highlighted by dashed lines 630 of the side lobe response. Signals of the desired main lobe 610 fall in the notch of the characteristic of the second apodization function 620. In this way, the clutter signals of the side lobes 630 are selected and isolated from the signals of the main lobe 610. The unwanted values from the side lobe response 630 are then subtracted from the image data obtained using the first apodization function 410 with the response shown in FIG. 8a. The result is signals mainly returned from the main lobe response 520, and the signals of the side lobes 530 of the lobe pattern have been substantially eliminated, meaning that the resulting signal used for imaging is primarily signals from the main lobe response of the lobe characteristic. In this way, sidelobe clutter is substantially removed from the ultrasound image.

The shape of the second apodization function, shown in graph 420 of FIG. 7b, may be altered to change the width of the null function 560 in the second image data. In this way, the angular spread of the remaining signals may be controlled. By reducing the width of this notch function, the spatial resolution of the final ultrasound image may be increased.

Figure 10:
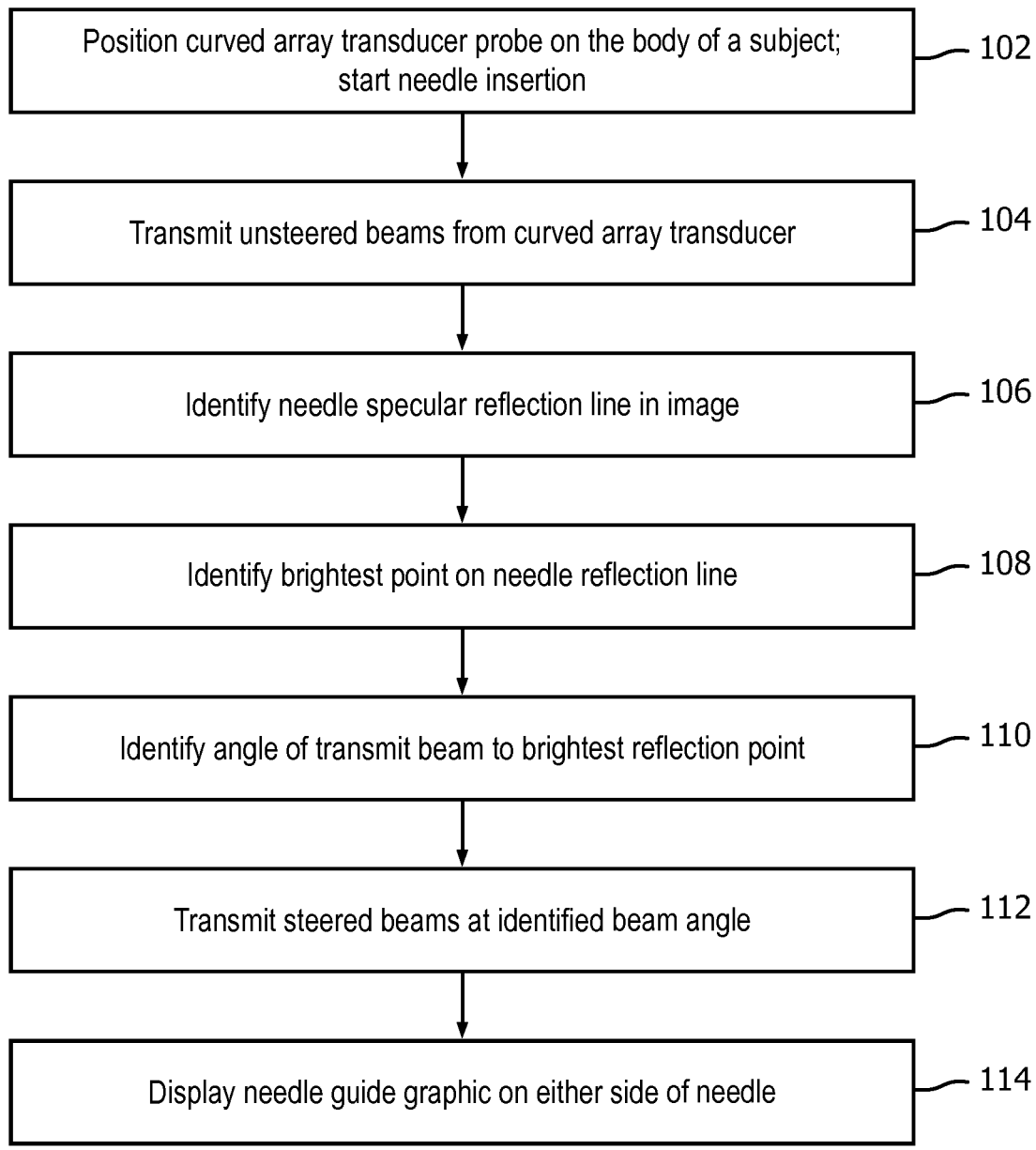
FIG. 10 is a flowchart of an ultrasound image guided needle insertion procedure conducted in accordance with the principles of the present invention.

An ultrasound image-guided needle insertion procedure in accordance with the present invention is outlined in FIG. 10. A clinician begins the procedure by positioning a curved array transducer probe on the body of a subject, manipulating the probe until the target anatomy for the procedure is in the field of view. The target anatomy may be a cyst which is to be biopsied using a needle, for instance. With the target anatomy in view in the ultrasound image, the clinician starts inserting the needle in-line with the plane of the image, as stated in step 102. As the insertion proceeds, the curved array transducer transmits unsteered beams over the field of view to image the field and capture the insertion of the needle as stated in step 104. In step 106 the needle location processor of the ultrasound system identifies the line of specular needle reflections in the image, where the radially directed beams from the curved array are intersecting the needle around the most favorable angle. In step 108 the needle location processor identifies the brightest point along the needle reflection line, which identifies the angle of the transmit beam which produced that bright point as stated in step 110.

The needle location processor then causes the transmit controller to control the curved array transducer to transmit parallel steered beams toward the needle at the identified beam angle as stated in step 112. Scanning with the parallel steered beams produces the strongest image of the needle, and a needle guide graphic is displayed with the image in step 114, preferably on either side of the location of the needle in the ultrasound image. Clutter reduction may then be performed using one of the dual apodization processing techniques explained above.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, for example, the needle location processor 46 and the clutter processor 50, or components and controllers therein, also may be implemented as part of one or more computers or microprocessors. The computer or processor may include a computing device, an input device, a display unit and an interface, for example, for accessing the Internet. The computer or processor may include a microprocessor. The microprocessor may be connected to a communication bus, for example, to access a PACS system or the data network for importing images. The computer or processor may also include a memory. The memory devices such as the 3D image data memory 48 may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and transmission of ultrasound images as described above may include various commands that instruct a computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules such as a needle location module, a clutter module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. A method for operating an ultrasonic imaging system for image guidance of needle insertion in a subject, the method comprising:
    acquiring a first ultrasound image of an image field in the subject with a curved array transducer probe, the image field suspected of comprising a needle inserted into the subject, the ultrasound image comprising a plurality of echo returns from unsteered transmit beams impinging upon the needle at a plurality of different angles of incidence;
    identifying an angle of a transmit beam for producing a peak magnitude of echo return from the needle in the image field based on application of image processing to said ultrasound image echo returns;
    transmitting a plurality of parallel steered beams from the curved array transducer probe at the identified angle and receiving image data in response;
    processing the image data with two different apodization functions adapted to isolate clutter in the image data and forming two images, each using a different apodization function;
    correlating or combining pixel values of the two images processed with the two different apodization functions to produce clutter-reduced image data; and
    displaying a clutter-reduced ultrasound image of the needle in the image field;

wherein processing the image data with two different apodization functions comprises processing the image data with complementary apodization functions, wherein processing the image data with complementary apodization functions comprises processing the image data with apodization functions which affect side lobe artifact data differently, and wherein using image data processed with the two different apodization functions comprises combining image data having both side lobe and main lobe data with image data having only side lobe or main lobe data.

2. The method of claim 1, wherein processing the image data with apodization functions which affect side lobe artifact data differently comprises using an apodization function which acts as a notch filter for side lobe or main lobe data.

* * * * *